United States Patent
Sachse et al.

(10) Patent No.: US 6,191,272 B1
(45) Date of Patent: Feb. 20, 2001

(54) PROCESS FOR THE PREPARATION OF ENDO-NORTROPINE USING 8-BENZYL-NORTROPAN-3-ONE PERCHLORATE AS THE INTERMEDIATE, AS WELL AS THE LATTER SALT

(75) Inventors: Rolf Sachse, Berlin; Albert Schaupp, Strullendorf, both of (DE)

(73) Assignee: Dr. Robert Pfleger Chemische Fabrik, GmbH, Bamberg (DE)

( * ) Notice: Under 35 U.S.C. 154(b), the term of this patent shall be extended for 0 days.

(21) Appl. No.: 09/487,051

(22) Filed: Jan. 19, 2000

(30) Foreign Application Priority Data

Feb. 20, 1999 (EP) ................................................ 99103354

(51) Int. Cl.$^7$ ................................................ C07D 225/00
(52) U.S. Cl. .......................................... 540/450; 540/476
(58) Field of Search .......................... 514/211.01, 211.05; 540/450, 476

(56) References Cited

FOREIGN PATENT DOCUMENTS

| 1194422 | 6/1965 | (DE) . |
| 3546218 | 7/1987 | (DE) . |
| 0042705 | 12/1981 | (EP) . |

OTHER PUBLICATIONS

K.Nador et al, "N–AlkyInortrop. & their HO"Arzneimittle–Forsch. 12, 305–9(1962)/CAOLD;CA58:3384d, Jan. 1962.*
K. Nader et al. Chemical Abstracts, vol. 58, No. 4, 1963.

* cited by examiner

Primary Examiner—Mukund J. Shah
Assistant Examiner—Sudhaker B. Patel
(74) Attorney, Agent, or Firm—Roberts & Mercanti, LLP

(57) ABSTRACT

The invention relates to a process for the preparation of endo-nortropine using 8-benzyl-nortropan-3-one perchlorate, as well as the latter product. Endo-nortropine is the key product for the production of important azonia-spironortropanol esters, which are used as pharmaceuticals, particularly spasmolytics. There are three different synthesis methods for the preparation of said intermediate, which lead to different disadvantages. These problems are obviated by the present invention through the two-stage treatment of 8-benzyl-nortropan-3-one perchlorate with catalytically activated hydrogen, the starting product initially being pre-hydrogenated in aqueous suspension and at atmospheric pressure and ambient pressure with a palladium catalyst, at the end of the reaction the catalyst is recovered by filtration, the filtrate is passed over an anion exchanger and the now alkaline reacting solution is rendered turbulent at 1000 to 1500 r.p.m. with hydrogen activated by Raney nickel at atmospheric pressure and ambient temperature. This new synthesis method using the novel perchlorate salt as an intermediate is extremely economic and environmentally friendly and supplies substantially completely stereoselectively the desired endo-form of nortropine.

18 Claims, No Drawings

PROCESS FOR THE PREPARATION OF ENDO-NORTROPINE USING 8-BENZYL-NORTROPAN-3-ONE PERCHLORATE AS THE INTERMEDIATE, AS WELL AS THE LATTER SALT

BACKGROUND OF THE INVENTION

1. Field of the Invention

The invention relates to a process for the preparation of endo-nortropine using 8-benzyl-nortropan-3-one perchlorate as the intermediate, as well as the latter salt.

2. Description of the Related Art

The prior art discloses numerous processes for the preparation of endo-nortropine and the latter substance itself. Endo-nortropine is the key product for the production of important azoniaspironortropanol esters, which are used as pharmaceuticals, particularly spasmolytics (cf. particularly German patent 1 194 422), whereas 8-benzyl-nortropan-3-one perchlorate is not known.

Hitherto only the picrate, hydrochloride and hydrobromide of 8-benzyl-nortropan-3-one are known, but for which no further use possibilities exist. 8-benzyl-nortropan-3-one is also mentioned in EP-A1-42 705 as an intermediate in the production of azabicycloalkane derivatives, whose pharmacological activity is described.

In principle, there are three known process procedures for the preparation of endo-nortropine, namely the saponification of tropane alkaloids, such as nor-1-hyoscyamine, convolvine and convolamine. However, the saponification of three alkaloids is not profitable, because the starting products are rare and expensive. Thus, as is known tropine is oxidatively demethylated in order to prepare endo-nortropine. In addition, photochemical methods for the demethylation and demethylation with ethyl chloroformates are known, cf. e.g. DE-A1-35 46 218. However, it is a disadvantage of said dealkylation process that expensive and in part environmentally prejudicial chemicals have to be used as starting products, which in turn can only be produced with difficulty. The known processes mainly also operate with overpressure and are usually not stereoselective.

SUMMARY OF THE INVENTION

Therefore the problem of the present invention is to provide an alternative process for the preparation of endo-nortropine, which can be simply and rapidly economically performed and which is also environmentally friendly. A further aim is to be able to obviate the need for overpressure process stages, whilst still operating as stereoselectively as possible. This is intended to permit an economic preparation of trospium chloride.

Surprisingly this problem is solved by the aforementioned process, which is based on a two-stage treatment of 8-benzyl-nortropan-3-one perchlorate with catalytically activated hydrogen, the starting product being initially prehydrogenated in aqueous suspension at atmospheric pressure and ambient temperature with a palladium catalyst, at the end of the reaction the catalyst is recovered by filtration, the filtrate is passed over an anion exchanger and the now alkaline reacting solution is rendered turbulent with hydrogen activated by Raney nickel at atmospheric pressure and ambient temperature and at 1000 to 1500 revolutions per minute.

DETAILED DESCRIPTION OF THE PREFERRED EMBODIMENTS

Of particular significance for the present invention is the fact that as a novel substance 8-benzyl-nortropan-3-one perchlorate is initially prepared as an intermediate by the per se known Robinson-Schöpf method and subsequent addition of perchlorate acid and precipitation of the corresponding perchlorate salt.

The perchlorate is then treated in aqueous suspension and at ambient temperature of preferably 20° C. under normal pressure with catalytically activated hydrogen. A ready-to-use 10 palladium catalyst on activated carbon is used as the catalyst.

In the said process the benzyl group is split off and the substrate reacted to 3-nortropanone, which then dissolves as a perchlorate acid salt.

Following the filtering off of the catalyst the aqueous solution is passed over a strong basic anion exchanger of the styrene-divinyl benzene type having the counterion OH⁻.

The now basic, aqueous 3-nortropanone solution, on adding Raney nickel catalyst, is now hydrogenated with hydrogen to endo-nortropine.

The aqueous solution is then freed from the catalyst by filtration and carefully concentrated in vacuo. What is left is a crude endo-nortropine which, if necessary, is recrystallized from acetone.

Compared with the prior art, the advantages of the process according to the invention can be described as follows:

The process for the preparation of endo-nortropine obviates the need for the complicated dealkylation process, no matter what method is used and where in part expensive and in part environmentally prejudicial chemicals are used.

Working takes place throughout in aqueous solutions and the auxiliary products such as catalysts and ion exchangers can easily be separated and regenerated.

In the catalytic transfer of hydrogen hydrogenation takes place at ambient temperature and without pressure in both stages. This is particularly surprising, because all known processes operate with an overpressure.

None of the known processes is based on 8-benzyl-nortropan-3-one perchlorate for the purpose of producing 3-nortropanone.

As a result of the salt formation to the perchlorate, the tropane substances are extremely stable during processing.

Hereinafter preferred examples for the preparation of 8-benzyl-nortropan-3-one perchlorate and the endo-nortropine are described relative to the following formula flow diagrams of the inventive process.

Robinson-Schöpf reaction

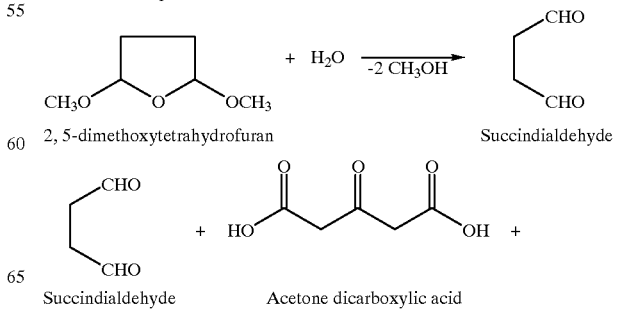

-continued

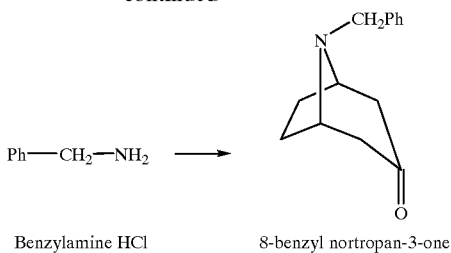

Benzylamine HCl      8-benzyl nortropan-3-one

Catalytic hydrogenation and anion exchange

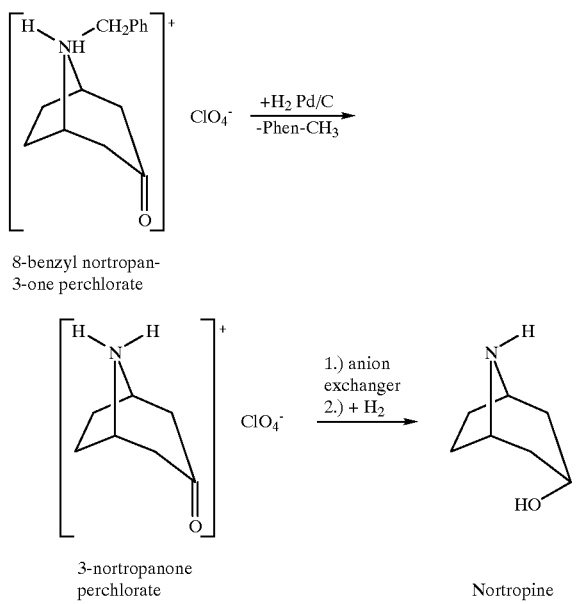

3-nortropanone perchlorate                    Nortropine

EXAMPLES

Example 1

Process for the preparation of 8-benzyl-nortropan-3-one perchlorate:

Accompanied by stirring, 51 g corresponding to 0.386 mole of 2,5-dimethoxytetrahydrofuran are mixed with 100 ml of water and on adding two 2 ml 25% hydrochloric acid portions ace hydrolyzed at ambient temperature to succindialdehyde. Following dilution with water to a volume of 400 ml, 58 g of acetone dicarboxylic acid are added to the stirred solution. A clear, yellow solution is obtained after stirring for 5 minutes and is now mixed portion-wise with 54.2 g of benzyl ammonium chloride, which rapidly dissolves accompanied by further stirring. The constantly stirred solution is now buffered to pH 2 with 12 g of sodium hydrogen phosphate and further stirred overnight.

The now cloudy solution is rendered clear by adding 4 g of activated carbon and filtration. Through the addition of 33 ml of 60% perchloric acid to the filtrate, the desired product is precipitated. It is suction filtered, washed acid-free with a little water and dried in air.

Yield: 87 g of crude product, HPLC content: 92.5%, melting point: 193 to 194° C.

Both the corresponding elementary analysis and the IR-spectrum confirm the newly found perchlorate salt.

Example 2

Hydrogenation of 8-benzyl-nortropan-3-one perchorate to endo-nortropine:

17.5 g of approximately 90% 8-benzyl-nortropan-3-one perchlorate are suspended in 180 ml of water. This is followed by the addition of 1.8 g of 10% palladium/activated carbon catalyst and hydrogenation at ambient temperature, under normal pressure with hydrogen. After 4 hours hydrogen absorption is ended. The catalyst is filtered off and the clear, colourless filtrate is passed over a column containing a strongly basic, gel-like anion exchanger of type 1 with the counterion OH$^-$. With an exchanger capacity of approximately 1.4 mmole/ml, approximately 40 ml thereof are required. This is followed by three 20 ml water portions, the collected eluates are mixed with 3 g of Raney nickel catalyst and the mixture rendered highly turbulent with hydrogen. When the hydrogen absorption is ended, the catalyst is separated and the clear filtrate concentrated in vacuo.

5.6 g of crude endo-nortropine with a melting point of 155 to 160° C. accompanied by decomposition, are left as a residue.

Tests have revealed that the yields are generally in the range 85 to 100% of theory.

What is claimed is:

1. A process for the preparation of endo-nortropine, comprising hydrogenating 8-benzyl-nortropan-3-one perchlorate with catalytically activated hydrogen by hydrogenating the 8-benzyl-nortropan-3-one perchlorate in aqueous suspension at atmospheric pressure and ambient temperature with a palladium catalyst, recovering the catalyst is by filtration, passing the filtrate over an anion exchanger to produce a now alkaline reactive solution and then turbulently reacting the alkaline reactive solution with hydrogen activated by Raney nickel at atmospheric pressure and ambient temperature and 1000 to 1500 revolutions per minute.

2. A process for the preparation of 8-benzyl-nortropan-3-one perchlorate comprising a. preparation of 8-benzyl-nortropan-3-one perchlorate according to the Robinson-Schöpf method from dimethoxytetrahydrofuran, benzyl amine and acetone dicarboxylic acid in aqueous solution, b. addition of an equimolar quantity of perchloric acid at ambient temperature and accompanied by the precipitation of the end product.

3. 8-benzyl-nortropan-3-one perchlorate.

4. The process according to claim 1, wherein the produced endo-nortropine is subsequently recrystallized from acetone.

5. The process according to claim 1, wherein the catalyst comprises 10% palladium on activated carbon.

6. A process for the preparation of endo-nortropine which comprises hydrogenating an aqueous suspension of 8-benzyl-nortropan-3-one perchlorate, passing the resulting aqueous solution over a basic anion exchanger to produce an aqueous 3-nortropanone solution, and then hydrogenating the 3-nortropanone solution to produce endo-nortropine.

7. The process of claim 6 wherein the hydrogenating of the aqueous suspension of 8-benzyl-nortropan-3-one perchlorate is conducted at atmospheric pressure and ambient temperatures.

8. The process of claim 6 wherein the hydrogenating of the aqueous suspension of 8-benzyl-nortropan-3-one perchlorate is conducted with a hydrogenation catalyst.

9. The process of claim 8 wherein the hydrogenation catalyst comprises palladium.

10. The process of claim 8 wherein the hydrogenation catalyst comprises palladium on activated carbon.

11. The process of claim 8 wherein after the hydrogenating of the aqueous suspension of 8-benzyl-nortropan-3-one perchlorate the catalyst is filtered off before the passing of the resulting aqueous solution over the basic anion exchanger.

12. The process of claim 6 wherein the hydrogenating of the 3-nortropanone solution is conducted with Raney nickel catalyst.

13. The process of claim 12 further comprising the subsequent step of removing the catalyst.

14. The process of claim 6 comprising the subsequent step of concentrating the endo-nortropine.

15. The process of claim 6 comprising the subsequent step of concentrating the endo-nortropine in vacuo.

16. The process of claim 15 comprising the subsequent step of recrystallizing the endo-nortropine.

17. The process of claim 15 comprising the subsequent step of recrystallizing the endo-nortropine from acetone.

18. The process of claim 6 wherein the yield of endo-nortropine ranges from about 85% to about 100%.

* * * * *